United States Patent [19]

Wilkins et al.

[11] Patent Number: 5,098,826
[45] Date of Patent: Mar. 24, 1992

[54] **DETECTION, ISOLATION AND PURIFICATION OF *CLOSTRIDIUM DIFFICILE* TOXIN A WITH TOXIN RECEPTORS**

[75] Inventors: Tracy D. Wilkins, Riner; Kenneth D. Tucker, Blacksburg, both of Va.

[73] Assignee: Virginia Tech Intellectual Properties, Inc., Blacksburg, Va.

[21] Appl. No.: 491,396

[22] Filed: Mar. 9, 1990

[51] Int. Cl.$^5$ .................. G01N 33/569; C12Q 1/04
[52] U.S. Cl. ..................... 435/7.32; 530/350
[58] Field of Search ............ 435/7.32, 38, 4; 530/350

[56] References Cited

U.S. PATENT DOCUMENTS 4,863,852 9/1989 Wilkins et al. ............ 435/7.25

OTHER PUBLICATIONS

Lyerly et al., J. Clin. Microbiol., 21, 12-14 (1985).
Lyerly et al., J. Clin. Microbiol., 17, 72-78 (1983).
Krivan et al., Infect. Immun., 53, 573-581 (1986).
Krivan et al., Infect. Immun., 55, 1873-1877 (1987).
Clark et al., Arch. Biochem. Biophys., 257, 217-229 (1987).
Lyerly et al., Clin. Microbial. Rev. 1, 1-18 (1988).

*Primary Examiner*—Robert A. Wax
*Assistant Examiner*—M. P. Woodward
*Attorney, Agent, or Firm*—Seidel, Gonda, Lavorgna & Monaco

[57] ABSTRACT

A method is provided for detecting the presence of *C. difficile* toxin A. Stool or other appropriate specimen is contacted with a reagent containing the human X, Y or I-antigens, each of which is a specific receptor for toxin A. The reagent may be intact cells, cell membranes, membrane fractions containing any of these antigens, glycoconjugates, as well as the purified oligosaccharide antigen per se. Binding of toxin A is determined by conventional assay techniques. The method may also be used to isolate and purify toxin A. Conversely, immobilized toxin A may be used to detect, isolate, or purify biological materials of interest expressing the X, Y or I antigens.

21 Claims, 5 Drawing Sheets

DETECTION, ISOLATION AND PURIFICATION OF *CLOSTRIDIUM DIFFICILE* TOXIN A WITH TOXIN RECEPTORS

REFERENCE TO GOVERNMENT GRANT

The invention is supported in part by grant AI 15749 from the National Institutes of Health.

FIELD OF THE INVENTION

The invention relates generally to the detection, isolation, and purification of *Clostridium difficile* toxin A. The invention also relates to the detection, isolation and purification of materials containing the human I, X or Y antigens which act as receptors for toxin A.

DEFINITIONS

The following sugars are represented by their customary abbreviations:

| | |
|---|---|
| Gal | galactose |
| Glc | glucose |
| GlcNAc | N-acetyl glucosamine |
| Fuc | fucose |
| Man | Mannose |
| LNF III | Lacto-N-fucopentose |
| LNnH | Lacto-N-neo-hexose |

BACKGROUND OF THE INVENTION

*Clostridium difficile* causes disease within the gastrointestinal tract, usually following an alteration of the intestinal microecology. The pathogenic role of toxigenic *C. difficile* in antibiotic-associated pseudo-membranous colitis in humans is well established. Disease symptoms vary with the source of the pathogen, antibiotic exposure, toxin production, and patient age.

*C. difficile* produces two toxins, designated A and B. The toxins are implicated in the etiology of the disease. Toxin A is primarily an enterotoxin with slight cytotoxic activity, whereas toxin B is a potent cytotoxin. Toxin A causes extensive damage to the gut mucosa, as well as accumulation of fluid in the intestinal tract. It is believed that the primary event in the mechanism of *C. difficile* infection involves the specific binding of toxin to receptors on the intestinal cell surface.

*C. difficile*-associated intestinal disease has been reported in infants, and in adults in the absence of antibiotic therapy. Moreover, *C. difficile* is one of the most common bacterial enteropathogens found in stool specimens in hospitals. The organism has been reported to be one of the most commonly detected bacterial pathogens of enteric disease.

*C. difficile* causes pseudomembranous colitis in humans as a result of the elimination of the normal flora of the colon by antibiotic usage, and growth of this toxin-producing bacterium. The disease usually occurs in hospitalized patients where it causes a massive diarrhea with extensive inflammation of the colon. Mortality rates as high as 44% have been reported for this disease. Treatment is based on a proper diagnosis which is accomplished by establishing the presence of the toxin and demonstrating the characteristic lesions in the colon.

One method for detecting pathogenic *C. difficile* involves the culture of human feces, which requires specialized facilities for a long period of incubation. This test suffers from interference by non-pathogenic *C. difficile* strains, namely strains not producing toxin. The test is costly, time-consuming, and can only be performed in larger, well-equipped hospitals or in private laboratories.

Specific antisera to toxin A have been used to detect toxin A by means of an enzyme-linked immunosorbent assay (ELISA). Lyerly, et al., *J. Clin. Microbiol.* 17, 72–78 (1983). Similarly, the resulting immobilized antibody agglutinates soluble toxin A. The agglutination of the large latex beads may be visualized, indicating the presence of toxin A in the sample.

Lyerly et al., *J. Clin. Microbiol.* 21, 12–14 (1985) disclose a monoclonal antibody, affinity-purified polyclonal antibody and monospecific antiserum against toxin A as possible immunodiagnostic reagents for *C. difficile* disease.

U.S. Pat. No. 4,863,852 describes a method for isolating, detecting and purifying *C. difficile* toxin A utilizing a biological receptor for toxin A comprising a reagent containing the terminal oligosaccharide sequence Gal$\alpha$(1→3)Gal$\beta$(1→4)GlcNAc. The carbohydrate does not exist on human cells. Maximal binding of the toxin A to the Gal$\alpha$(1→3)Gal$\beta$(1→4)GlcNAc receptor occurs at 4° C. At 37° C., binding is not detected.

SUMMARY OF THE INVENTION

We have found that in addition to binding the non-human receptor Gal$\alpha$(1→3)Gal$\beta$(1→4)GlcNAc, toxin A is capable of specific reversible binding to human antigens X, Y and I, none of which contain the $\alpha$(1→3)-linked terminal galactose of the animal receptor.

Thus, *C. difficile* enterotoxin (toxin A) may be detected and/or purified by contacting a sample suspected of containing the toxin with a reagent comprising one or more of the terminal non-reducing structures which characterize antigens X, Y or I. The terminal non-reducing portion of the X antigen recognized by toxin A, which antigen is also known as "LNF III" or "Le$^X$", comprises the trisaccharide:

$$\text{Gal}\beta(1\rightarrow4)\text{GlcNAc} \quad\quad (I)$$
$$\underset{\text{Fuc}\alpha1}{\overset{3}{\uparrow}}$$

The terminal non-reducing structure characterizing the Y antigen, which antigen is also known as "Le$^Y$", comprises the branched tetrasaccharide:

$$\text{Gal}\beta(1\rightarrow4)\text{GlcNAc} \quad\quad (II)$$
$$\underset{\text{Fuc}\alpha1}{\overset{2}{\uparrow}} \quad \underset{\text{Fuc}\alpha1}{\overset{3}{\uparrow}}$$

The terminal non-reducing structure of the I antigen, which antigen is also known as "LNnH", comprises the branched hexasaccharide:

$$\text{Gal}\beta(1\rightarrow4)\text{GlcNAc}\beta(1\rightarrow3)\text{Gal}\beta(1\rightarrow4)\text{Glc} \quad (III)$$
$$\underset{\text{Gal}\beta(1\rightarrow4)\text{GlcNAc}\beta1}{\overset{6}{\uparrow}}$$

Quantitative binding of toxin A to these structures occurs rapidly, specifically, reliably, and reversibly in a dose-dependent manner. The structures are specific for binding toxin A, and do not cross-react with the related C. difficile toxin, toxin B. The antigens can therefore be used for large-scale purification of toxin A, as well as for the detection and isolation of minute toxin A quantities.

A method for detecting C. difficile toxin A comprises (a) contacting a specimen with a reagent comprising the terminal non-reducing structure of any of antigens X, Y or I, and (b) assaying for binding of C. difficile toxin A to the reagent.

Conversely, toxin A is used according to the invention to detect the X, Y or I antigens, or to isolate and/or purify biological materials containing the terminal non-reducing structures of the X, Y or I antigens. The biological materials can be detected and/or purified even when present in very small quantities because of the specificity, reliability and reversibility of the antigen binding to toxin A.

A method for isolating or purifying the X, Y or I antigens, or isolating or purifying biological materials containing the terminal non-reducing structure characteristic of any of these antigens, comprises (a) contacting a source of the antigen-containing biological material with immobilized C. difficile toxin A at a temperature favoring reversible binding of the material to toxin A; (b) increasing the temperature or pH to release the antigen-containing material from the immobilized toxin A; and (c) eluting the material.

Conversely, a method for isolating or purifying toxin A comprises contacting a source of toxin A with an immobilized reagent containing the terminal non-reducing structure characteristic of any of antigens X, Y or I at a temperature favoring reversible binding of toxin A to the immobilized reagent; (b) increasing the temperature or pH to release the toxin A bound to the immobilized reagent; and (c) eluting toxin A.

Binding is temperature dependent. It is therefore preferably carried out in the cold, or using cold reagents. Generally, the binding reaction occurs favorably below room temperature (about 20° C.). Temperatures of 0°-15° are preferred, 4° C. being most preferred. Upon warming above room temperature, the toxin begins to disassociate from the antigen in an undenatured form. For the X and I antigens, warming to about 30° C. or higher will release most of the toxin, with 30°-37° C. being preferred. At 37° C. no toxin A binding to the X or I antigen is detected. For the Y antigen, warming to about 37° C. or higher will release only about 80% of the toxin. Increasing the temperature will result in further release of toxin A.

The result of this reversible binding is a rapid one step purification technique for toxin A, as well as for purification of the X, Y or I antigens, or biological materials expressing these antigens. The purification process provides very high yields of very pure product.

Unlike the X and I antigens, and unlike the Gal$\alpha$(1→3)Gal$\beta$(1→4)GlcNAc receptor described in U.S. Pat. No. 4,863,852, the Y antigen reversibly binds significant amounts of toxin A at temperatures as high as 37° C. The high affinity of toxin A for the Y antigen at 37° C. makes this antigen useful in applications for which the other toxin A receptors are not suitable. In particular, the detection and purification methods described herein utilizing toxin A binding to the Y antigen may be carried out at room or higher temperature, without adverse consequence.

By "reagent" with regard to any of the terminal non-reducing oligosaccharide structures of formulas I, II or III is meant the receptor for toxin A containing such oligosaccharides whether or not the receptor is in the free carbohydrate form, or present as part of a naturally occurring glycolipid or glycoprotein; or as conjugated to or otherwise affixed to a natural or chemically synthesized carrier, molecule, cell, membrane, bead, liposome, solid support (synthetic or natural), or the like; or as contained in any other material expressing, or having affixed thereto, the receptor structure in a form available for binding to toxin A.

By "biological material" is meant tissues, cells, cell fragments, culture filtrate, molecules or the like.

By "specimen" is meant any preparation containing tissue, cells, blood, stool, fluid or other material that may contain C. difficile toxin A.

DETAILED DESCRIPTION OF THE INVENTION

Figure 1A:
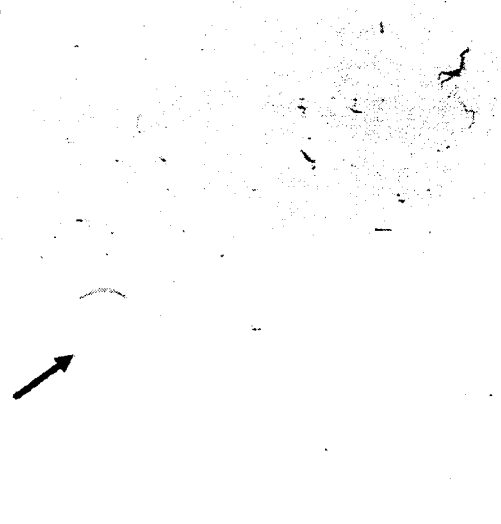
FIG. 1 is a photograph of a stained gel of the crossed immunoelectrophoresis of (A) C. difficile toxin A, and (B) a mixture C. difficile toxin A and a human serum albumin conjugate of the X antigen (LNF III-HSA).

We have found that the human antigens X, Y and I specifically and reversibly bind C. difficile toxin A. Unlike the Gal$\alpha$(1→3)Gal$\beta$(1→4)GlcNAc receptor identified in U.S. Pat. No. 4,863,852, these antigens do not contain the non-reducing terminal $\alpha$(1→3)-linked galactose moiety. Moreover, while the X, Y, and I antigens comprise human antigens found on a variety of human cells, the toxin A receptor of the aforesaid patent does not exist in normal human cells.

Blood group specificities are major alloantigenic systems in human tissues Many of the specificities are carried by two types of backbone structures. Type 1 chains contain Gal$\beta$(1→3)GlcNAc, while Type 2 chains contain Gal$\beta$(1→4)GlcNAc. Fucosylation of the Type 2 chain leads to expression of, among other things, the X and Y antigens.

The X and Y antigens, also known as "Le$^X$" and Le$^Y$", respectively, are also expressed in a variety of tumors. See Sakamoto et al., *Cancer Research* 46, 1553-1561 (1986). Abe et al., *Cancer Research* 46, 2639-2644 (1986), suggest that Y antigen expression may be a marker for diagnosis of colonic cancer. The X antigen, also known as stage-specific embryonic antigen (SSEA-1), is widely distributed in man on epithelial cells and on secreted glycoproteins.

Oligosaccharides corresponding to the X and Y antigens are commercially available. They may be isolated from their relevant biological sources, e.g. human milk, such as by absorption with anti-X or anti-Y monoclonal antibodies. See Rettig et al., *Cancer Res.* 45, 815–821 (1985) (anti-X and anti-Y monoclonal antibodies); Solter et al., *Proc. Natl. Acad. Sci. USA* 75, 5565–5569 (1978) (anti-X monoclonal antibody); Abe et al., *Cancer Research* 46, 2639–2644 (1986) (anti-Y monoclonal antibody). Alternatively, the X and Y antigens may be chemically synthesized accordingly to the teachings of Hindsgaul et al., *Carbohydrate Research* 109, 109–142 (1982), the entire disclosure of which is incorporated herein by reference.

The I antigen, also known as "LNnH" antigen, is another Type 2 antigen. Its expression is developmentally-regulated on adult human lymphocytes. It replaces the LNnT antigen also known as "i-antigen" one year after birth. The i-antigen is expressed as the linear oligosaccharide Gal$\beta$(1→4)GlcNAc$\beta$(1→3)Gal$\beta$(1→4)Glc, while the I antigen comprises the branched structure:

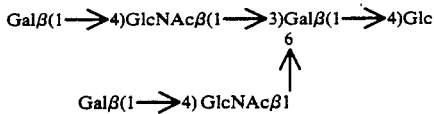

The I antigen may be obtained from any of its biological sources, e.g. human milk, by absorption with anti-I monoclonal antibodies. See Feizi et al., *J. Exp. Med.* 149, 975–980 (1979). Oligosaccharide corresponding to the I antigen is commercially available.

Any suitable material containing the characteristic terminal non-reducing oligosaccharide structure of the X, Y or I antigens may be employed as the toxin A binding reagent according to the present invention to detect, isolate or purify toxin A. The reagent may comprise purified oligosaccharide, or oligosaccharide conjugated to a lipid or protein, as in the naturally occurring glycolipids or glycoproteins expressing the X, Y or I antigens. The reagent may further take the form of a conjugate of the purified oligosaccharide with a chemically synthesized or natural carrier, e.g., human serum albumin, or oligosaccharide linked to any synthetic or natural solid support. The form of the particular reagent is not critical, so long as the terminal non-reducing receptor structure of the antigen is available for binding toxin A.

The method of this invention for detecting, isolating or purifying toxin A, or conversely, for using toxin A to detect, isolate or purify biological materials expressing X, Y or I antigens, is a gentle, efficient, single-step procedure that yields highly purified product. The process can be scaled up to isolate or purify gram quantities of product within a few hours.

Generally, any suitable method for contacting the aforementioned oligosaccharide antigens and an appropriate specimen may be employed to detect, isolate or purify toxin A. Conversely, any suitable method for contacting toxin A and the antigens may be employed to detect, isolate or purify the latter. The binding reaction is almost instantaneous. Incubation times from 1–5 minutes are possible, although it is preferred to incubate for 5 minutes to insure complete binding.

To test specimens for the presence of toxin A, a reagent containing the oligosaccharide antigen, i.e., either X, Y or I, is contacted with the specimen. The extent of toxin A binding is determined by suitable assay. Binding may be assayed by a wide variety of well-known techniques including ELISA, hemagglutination, slide agglutination, slide coagglutination, latex agglutination, surface immobilization and entrapment of the toxin A receptor on particles (e.g., liposomes), indirect immunofluorescence, radioimmunoassay, crossed immunoelectrophoresis, and other techniques known to those skilled in the art.

The preferred assay for detecting the binding of toxin A to the oligosaccharide antigen is an ELISA, as for example, the ELISA more particularly described in Example 2, infra. A sandwich-type ELISA may also be effectively utilized, relying on monoclonal antibody, affinity-purified antibody or monospecific polyclonal antisera to toxin A. Any of these antibody preparations may be formed according to *J. Clin. Microbiol.* 21, 12–14 (1985) (monoclonal antibody and monospecific polyclonal antiserum) and Lyerly et al., *J. Clin. Microbiol.* 17, 72–78 (1983) (affinity purified toxin A antibody), the entire disclosures of which are incorporated herein by reference.

According to the teachings of the aforementioned references, monospecific toxin A antiserum and affinity-purified toxin A antibody may be prepared as follows:

PREPARATION OF MONOSPECIFIC TOXIN A ANTISERUM

A one year old Alpine Nubian male goat is injected with toxoid A mixed 1:1 with incomplete Freund adjuvant. The goat receives ca. 1 mg of toxoid A subcutaneously once each week for 4 weeks; it is then injected with active toxin A bound to Affi-Gel 10 (Bio-Rad Laboratories). The goat receives 1 ml of a 10% suspension of the toxin A-gel (ca. 0.1 mg of toxin A protein) once each week for 6 weeks. The antiserum is brought to 50% saturation with a solution of 100% saturated $(NH_4)_2SO_4$. The precipitate is collected, dissolved in phosphate-buffered saline (PBS) to the original sample volume, and dialyzed against PBS. The preparation is passed through a 0.45 μm membrane and stored at 4° C.

PREPARATION OF AFFINITY-PURIFIED TOXIN A ANTIBODIES

Goat antiserum (1 ml) against crude *C. difficile* toxin preparations is dialyzed against 1 liter of $NaHCO_3$—NaCl buffer overnight at 4° C. The dialyzed material is applied to a column (1×12 cm) of toxin A-Sepharose, and the column is washed with the $NaHCO_3$—NaCl buffer until there is no measurable absorbance at 280 nm. Antibodies bound to the gel are eluted by applying 2 ml of 2.5M KSCN (pH 6.8) to the column and washing with $NaHCO_3$—NaCl buffer. About 2 bed volumes of eluate are collected and concentrated to 1 ml with a Minicon-B15 concentrator (Amicon Corp., Lexington, Mass.). The eluate is washed twice (4 ml per wash) on a Minicon-B15 concentrator with physiological saline (pH 7.4).

According to a first ELISA technique for assaying binding of toxin A to the X, Y or I antigen, a reagent comprising the terminal non-reducing structure of any of said antigens is adhered to a solid support. The adhered reagent is incubated with a specimen containing an unknown amount of toxin A to immobilize the toxin A thereto. The immobilized toxin A is contacted with an enzyme-labelled anti-toxin A antibody and a substrate for the enzyme. The amount of toxin A in the specimen is determined from the extent of enzymatic conversion of the substrate.

According to a second ELISA technique for assaying binding of toxin A to the X, Y or I antigen, the specimen containing an unknown concentration of toxin A is incubated with anti-toxin A antibody adhered to a solid support to immobilize the toxin A contained in the specimen. The latter is contacted with a reagent comprising the terminal non-reducing structure of the X, Y or I antigens linked to a carrier. The immobilized toxin A is then contacted with an enzyme-labelled antibody to the carrier and a substrate for the enzyme. The amount of toxin A in the specimen is determined from the extent of enzymatic conversion of the substrate.

By "enzyme-labelled antibody" is meant to include any antibody whereby an enzyme is linked or linkable thereto by any suitable linking means. Thus, included in the definition of enzyme-labelled antibody is not only antibodies wherein the enzyme is affixed directly thereto, but also the situation by which the enzyme is linked or linkable to the antibody through intermediate linking means, such as in the case of the coupling of a biotin-labelled antibody to an avidin-labeled enzyme.

According to the second ELISA method, a sample containing an unknown toxin A concentration is added to a microtiter plate or other suitable support coated with monoclonal antibody, affinity-purified antibody or monospecific polyclonal antiserum to toxin A and incubated for 1 hour at 4° C. to permit adherence of the antibody to the plate wells. Oligosaccharide antigen (X, Y or I) conjugated to a suitable carrier, e.g., human serum albumin (HSA), is added to the plate, and the immobilized toxin A is allowed to bind to the antigen for 60 minutes at 4° C. HSA-conjugates of the X, Y and I antigens are commercially available from BioCarb Chemicals (Lund, Sweden). An enzyme-labelled secondary antibody to the carrier, i.e., anti-HSA antibody, is added to the plate, and incubated for 60 minutes at 4° C. Hydrolysis of a chromogenic substrate for the enzyme reaction proceeds until the assay is complete. For the X and I antigens, the assay step should be conducted at a temperature which will not result in the release of the toxin A from the plate, e.g. 4° C. For the Y antigen, the enzyme reaction is preferably conducted at, 4° C., but may be conducted at a temperature as high as 37° C., since the Y antigen binds toxin A even at this high temperature.

Any form of solid support may be used in place of the microtiter plate described in the above ELISA procedure. Thus, for example, the primary anti-toxin A antibody (monoclonal or polyclonal) may be coated onto a permeable membrane, in lieu of a microtiter plate, or may be applied to any other suitable solid phase support.

As an alternative to an ELISA, which utilizes an enzyme-labelled secondary antibody and the hydrolysis of a substrate to signal the presence of toxin A, any other form of labelling technique for signaling the occurrence of toxin A binding to the antigen may be utilized, e.g., fluorescent or luminescent dye. Thus, the assay may advantageously comprise a fluorescence assay, a luminescence assay, or the like.

Toxin A binding may be detected utilizing an agglutination assay of the type described in Example 3, infra.

X, Y or I antigen is immobilized by conventional techniques on a particulate support, e.g., red blood cells, latex, liposomes, or the like. A sample solution suspected of containing toxin A is mixed with the immobilized antigen. Following gentle rocking for 2 minutes at 4° C., antibody to toxin A, preferably monoclonal antibody, is added to the mixture to enhance agglutination. The mixture is gently rocked for an additional 2 minutes at 4° C. Agglutination of the particles may be observed visually.

To purify toxin A, any of the three oligosaccharide antigens may be immobilized on an insoluble matrix, e.g., silica gel, agarose, latex beads, or the like, to form an affinity resin using established procedures that are compatible with attaching the oligosaccharide to the particular matrix chosen. The receptor coupled to the matrix may be in the form of a naturally occurring glycolipid or glycoprotein containing any of the antigens X, Y or I, or may comprise the corresponding free oligosaccharide, either chemically synthesized or obtained from natural sources. Alternatively, the receptor may take the form of any of the three oligosaccharides corresponding to X, Y or I coupled to a chemically synthesized or biological carrier, e.g., HSA. Accordingly, a crude solution containing toxin A, e.g. *C. difficile* toxin A culture filtrate, is buffered to pH 6.0 and chilled to 4° C. The solution is passed over the affinity resin at 4° C. to bind the toxin. The resin is then washed with a suitable buffer, e.g., 0.05 M 2-[N-morpholino]ethanesulfonic acid (MES) buffer containing 0.15M NaCl pH 6.0. The resin is then warmed to 37° C., and the toxin is eluted in substantially pure, highly concentrated form by washing the resin with 0.05M 3-[N-morpholino]propanesulfonic acid (MOPS) buffer containing 0.15M NaCl pH 8.0 at 37° C.

The X and I antigens bind small amounts of toxin A relative to the Y antigen. Therefore the X and I antigens are useful for small scale purification of toxin A. The Y antigen, which binds greater amounts of toxin A, is better suited for large scale purification of toxin A. The Y antigen binds 50 to 100 fold more toxin A than the other toxin A receptors.

The test for detecting the presence of toxin A is advantageously performed on a culture filtrate from a culture of suspected *C. difficile*. Fecal material specimens are prepared as follows. Fecal specimens are diluted in an equal volume of phosphate buffered saline (PBS), pH 7.4 and kept frozen at −20° C. until used. The specimens are centrifuged for 15 minutes at 15,000× g, and the supernatant is tested for the presence of toxin A according to the method of the present invention.

The test for detecting the presence of toxin A may also be performed on specimens comprising the purported C. difficile organism per se, namely cultured cells isolated from patient feces. Thus, the test specimen may advantageously take the form of a scraping of a colony of suspected bacterium growing on agar medium or other solid surface, or may take the form of an aliquot of a culture of the bacterium growing on a liquid medium.

The following non-limiting examples illustrate the practice of the invention.

Selectivity of toxin A binding to HSA-conjugated X, Y and I antigen was demonstrated by crossed immunoelectrophoresis (X-IEP) according to Example 1, infra, and also by ELISA according to Example 2, infra. The HSA-conjugated carbohydrates identified in Table 1, infra, were obtained from BioCarb Chemicals (Lund, Sweden), and assayed for toxin A binding ability. In addition, the human proteins carcinoembryonic antigen (CEA) and secretory component (SC) were similarly assayed for toxin A binding, as they are known to contain the X antigen. Mizoguchi et al., *J. Biol. Chem.* 257, 9612-9621 (1982) (SC); Chandkrasekaran et al., *J. Biol. Chem.* 258, 7213-7222 (1983) (CEA). Bovine thyroglobulin, a naturally occurring glycoprotein containing the toxin A binding terminal sequence Gal$\alpha$(1→3)Gal$\beta$(1→4)GlcNAc, was used as a positive control.

Toxin A for these experiments was obtained from *C. difficile* VPI strain 10463. The organism was cultured, and the toxin A was purified from the culture filtrate as described in U.S. Pat. No. 4,863,852. Affinity-purified antibody to toxin A was prepared according to Lyerly et al., *J. Clin. Microbiol.* 17, 72-78 (1983) and biotinylated as follows: Five $\mu$l of 10 mg/ml of biotinamidocaproate N-hydroxysuccinimide ester (Sigma Chemical Co., St. Louis, Mo.) in dimethylsulfoxide was added to 200 $\mu$l of 1 mg/ml affinity-purified antibody to toxin A in phosphate-buffered saline (PBS) (0.02M sodium phosphate, 0.13M NaCl, pH 7.2). The mixture was incubated for 4 hours at room temperature. The free biotin was separated from the biotin-antibody conjugate, and the conjugate was utilized at 1:1000 dilution.

mixed and incubated on ice for 10 minutes, then 5 $\mu$l of this mixture was assayed by X-IEP for toxin A binding on a 5×5 cm glass slide substantially as described by Lyerly et al., *J. Clin. Microbiol.* 17, 72-78 (1983). Briefly, wells (1 mm in diameter) were cut in gels composed of 1.2% (wt/vol) low electroendosmotic agarose (Sigma Chemical Co.) in 0.025M Tris-Tricine buffer (0.6 g agarose in 50 ml buffer) (pH 8.6). The Tris-Tricine buffer is prepared by combining the following and adding deionized water up to a volume of 1 L: Tris, 9.8 g; Ca-lactate, 0.106 g; Tricine, 4.3 g; NaN$_3$, 0.2 g. For the first dimension, oligosaccharide-HSA sample (5 $\mu$l) was placed in a sample well in the lower corner of the plate. 0.1% bromphenol blue was placed in an upper corner well as a tracing dye, and the plate was subjected to electrophoresis at 10 V/cm at constant current and 4° C. The second dimension of the plate consisted of a 1.2% (wt/vol) agarose gel containing 0.1 ml of goat antiserum to C. difficile culture filtrate. Electrophoresis was performed at 10 V/cm for about 3 hours at 4° C. Gels were washed in 20 mM sodium phosphate with 130 mM NaCl, pH 7.4, stained with a staining solution (5 g Coomassie Blue R-250, 450 ml EtOH, 1000 ml glacial acetic acid, and 450 ml deionized H$_2$O), and de-stained in the staining solution minus Coomassie Blue. The results of the X-IEP assay are shown in Table 1.

EXAMPLE 1

Crossed Immunoelectrophoresis

100 $\mu$g toxin A and 500 $\mu$g/ml of each of the oligosaccharide-HSA conjugates of Table 1 in PBS were

TABLE 1

| OLIGOSACCHARIDE-HSA CONJUGATES | | TOXIN A BINDING ASSAY | Toxin A Binding | |
|---|---|---|---|---|
| Oligosaccharide | Trivial Name | Chemical Structure of Oligosaccharide | X-IEP | ELISA |
| LNF | Le$^d$, O$_1$ | Gal$\beta$(1→3)GlcNAc$\beta$(1→3)Gal$\beta$(1→4)Glc<br>2<br>↑<br>Fuc$\alpha$1 | − | − |
| LNF II | Le$^a$ | Gal$\beta$(1→3)GlcNAc$\beta$(1→3)Gal$\beta$(1→4)Glc<br>4<br>↑<br>Fuc$\alpha$1 | − | − |
| LND | Le$^b$ | Gal$\beta$(1→3)GlcNAc$\beta$(1→3)Gal$\beta$(1→4)Glc<br>2   4<br>↑   ↑<br>Fuc$\alpha$1  Fuc$\alpha$1 | − | − |
| LNF·III | Le$^x$, X | Gal$\beta$(1→4)GlcNAc$\beta$(1→3)Gal$\beta$(1→4)Glc<br>3<br>↑<br>Fuc$\alpha$1 | + | + |
| — | Le$^y$, Y | Gal$\beta$(1→4)GlcNAc<br>2   3<br>↑   ↑<br>Fuc$\alpha$1  Fuc$\alpha$1 | + | + |
| LNnT | i | Gal$\beta$(1→4)GlcNAc$\beta$(1→3)Gal$\beta$(1→4)Glc | − | − |

TABLE 1-continued

TOXIN A BINDING ASSAY

| OLIGOSACCHARIDE-HSA CONJUGATES | | | Toxin A Binding | |
|---|---|---|---|---|
| Oligosaccharide | Trivial Name | Chemical Structure of Oligosaccharide | X-IEP | ELISA |
| LNnH | I | Galβ(1→4)GlcNAcβ(1→3)Galβ(1→4)Glc<br>                                           6<br>                                           ↑<br>                         Galβ(1→4)GlcNAcβ1 | + | + |
| BiAO | — | Galβ(1→4)GlcNAcβ(1→2)Manα(1→3)Manβ(1→4)GlcNAc<br>                                                      6<br>                                                   ↑<br>                    Galβ(1→4)GlcNAcβ(1→2)Manα1 | — | — |
| OTHER<br>Thyroglobulin | | Galα(1→3)Galβ(1→4)GlcNAc | + | + |
| Secretory Component | | Galβ(1→4)GlcNAc<br>              3<br>              ↑<br>              Fucα1 | + | + |
| Carcinoembryonic Antigen | | Galβ(1→4)GlcNAc<br>              3<br>              ↑<br>              Fucα1 | + | + |

Of the oligosaccharide-HSA complexes tested, only the complexes with the X, Y and I antigens caused an alteration in the migration of toxin A on cross plates. The fact that the other oligosaccharide-HSA conjugates did not alter the migration of toxin A demonstrates the specificity of the toxin for certain specific oligosaccharides, and demonstrates that the binding of the toxin is specific for the oligosaccharide and not the HSA carrier.

Figure 1B:
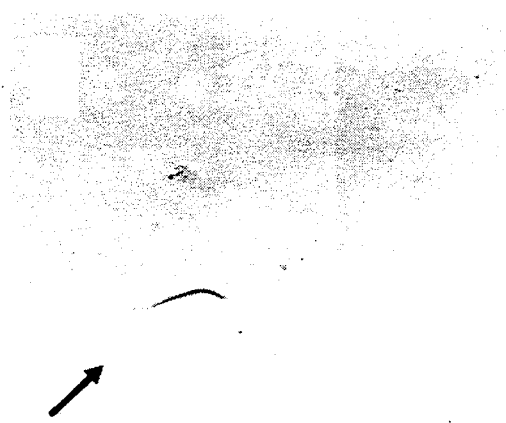
Figure 2A:
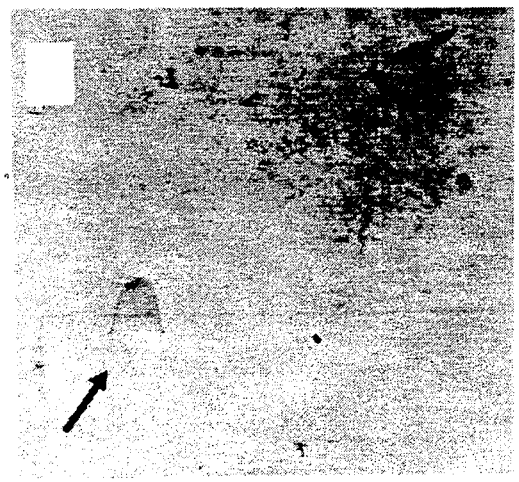
FIG. 2 is a photograph of a stained gel of the crossed immunoelectrophoresis of (A) C. difficile toxin A, and (B) C. difficile toxin A and a human serum albumin conjugate of the Y antigen (Le$^Y$-HSA).
Figure 2B:
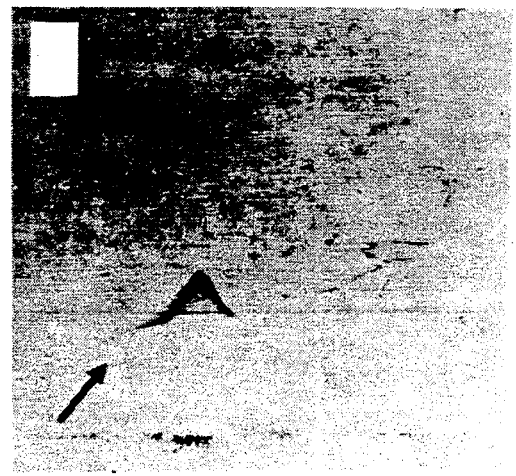

The altered migration pattern of toxin A in X-IEP upon incubation with an HSA conjugate of the X antigen is apparent from FIG. 1. FIG. 1A shows the migration of the toxin A peak from the electrophoresis origin, indicated by the arrow. Electrophoresis in the presence of conjugate (LNF III-HSA) resulted in displacement of the toxin A peak, as shown in FIG. 1B. Similarly, the altered migration of the toxin A in the absence (FIG. 2A) and presence (FIG. 2B) of an HSA conjugate of the Y antigen is shown in FIG. 2. The same behavior was observed upon electrophoresis in the presence of the HSA conjugate of the I antigen (LNnH-HSA), and in the presence of CEA or SC.

The principle behind the X-IEP assay is that the rate of migration of toxin A in an electric field is dependent on the net charge of the molecule, which is dependant on its isoelectric point and the pH of the electrophoresis medium. Toxin A has a slight negative charge at pH 8.6, which is the pH at which the X-IEP was carried out. The toxin migrates slowly in the applied electric field. HSA, on the other hand, has a relatively high net negative charge at pH 8.6. HSA migrates more rapidly in the electric field than toxin A. When toxin A is combined with an oligosaccharide-HSA conjugate capable of binding toxin A, the bound toxin migrates at an increased rate in the electric field because the rate of toxin A migration is now dependent on the net charge of the toxin/oligosaccharide-HSA complex. If the oligosaccharide-HSA which is electrophesed with the toxin A does not bind the toxin, then the rate of toxin A migration is unaffected.

While the I antigen was observed to bind toxin A, the two related carbohydrates, LNnT and BiOA did not bind the toxin. The ability of the I antigen to bind toxin A is surprising since Clark et al. Arch. Biochem. Biphys. 257, 217–229 (1987) have demonstrated that removal of the α-linked galactose from Galα(1→3-)Galβ(1→4)GlcNAcβ(1→3)Galβ(1→3)Glcβ1 prevents toxin A from binding to the resulting tetrasaccharide, which comprises the i-antigen. The i-antigen has a structure similar to the I antigen.

The ability of the Y antigen to bind toxin A is similarly surprising in view of Krivan et al., Infec. and Imm. 53, 573–581 (1986), disclosing that the presence of an α(1→2)-linked fucose on the galactose adjacent to the N-acetyl-glucosamine moiety prevents toxin A from binding to Galα(1→3)[Fucα(1→2)]Galβ(1→4)GlcNAc. Krivan et al. and U.S. Pat. No. 4,863,852 disclose that toxin A binds to Galα-(1→3)Galβ(1→4)GlcNAc, but does not bind Galα(1→3)[Fucα-(1→2)]Galβ(1→4)GlcNAc. The Y antigen contains a fucose moiety similarly linked α(1→2) to the same galactose.

EXAMPLE 2

Elisa

The wells of a polystyrene 96-well microtiter plate (Immulon type II; Dynatech Laboratories, Inc., Alexandria, Va.) were coated with serial 1:2 dilutions of (CEA, SC, thyroglobulin and the oligosaccharide-HSA conjugates of Table 1, starting at 10 μg/ml of each in 50 mM carbonate buffer (pH 9.6). 150 μl was added per well. Plates were incubated 16 hours at 4° C. then washed with PBS-T (0.8% NaCl, 0.02% $KH_2PO_4$, 0.22% $Na_2HPO_4$, 0.02% KCl, 0.05% Tween 20, 0.02% $NaN_3$, pH 7.4). The plates were blocked with 0.5% casein in Tris-buffered saline (TBS) (100 mM Tris, 150 mM NaCl, pH 7.0) for 1 hour at 22° C. The plates were washed twice with PBS-T. Toxin A at 10 μg/ml in PBS-T, 100 μl/well was added to the wells. The plates were incubated at either 4° C. or at 37° C. for 3 hours. After this point all buffers were at 4° C. and all treatments were performed in a 4° C. cold room, unless otherwise stated. The plates were washed twice, and 100 μl of a 1:1000 dilution of biotinylated antibody to toxin A in PBS-T was added to each well. The plates were incubated for 1 hour. The plates were then washed twice with PBS-T, and 100 μl of 0.1 U/ml of alkaline phosphatase conjugated to avidin (Sigma Chemical Co.) was added to each well. The plates were incubated for 1 hour, then washed twice. At this time the plates were moved to room temperature, and 100 μl of 1 mg/ml of p-nitrophenylphosphate in 100 mM diethanolamine buffer (pH 9.8) was added to each well. The plates were incubated for 90 minutes at room temperature. (Plates utilized in a pH dependence binding assay were incubated for 20 minutes.) The absorbance was read at 405 nm. Control wells included wells with either no toxin A and/or with no glycoconjugate. The results are summarized in Table 1.

Figure 3:
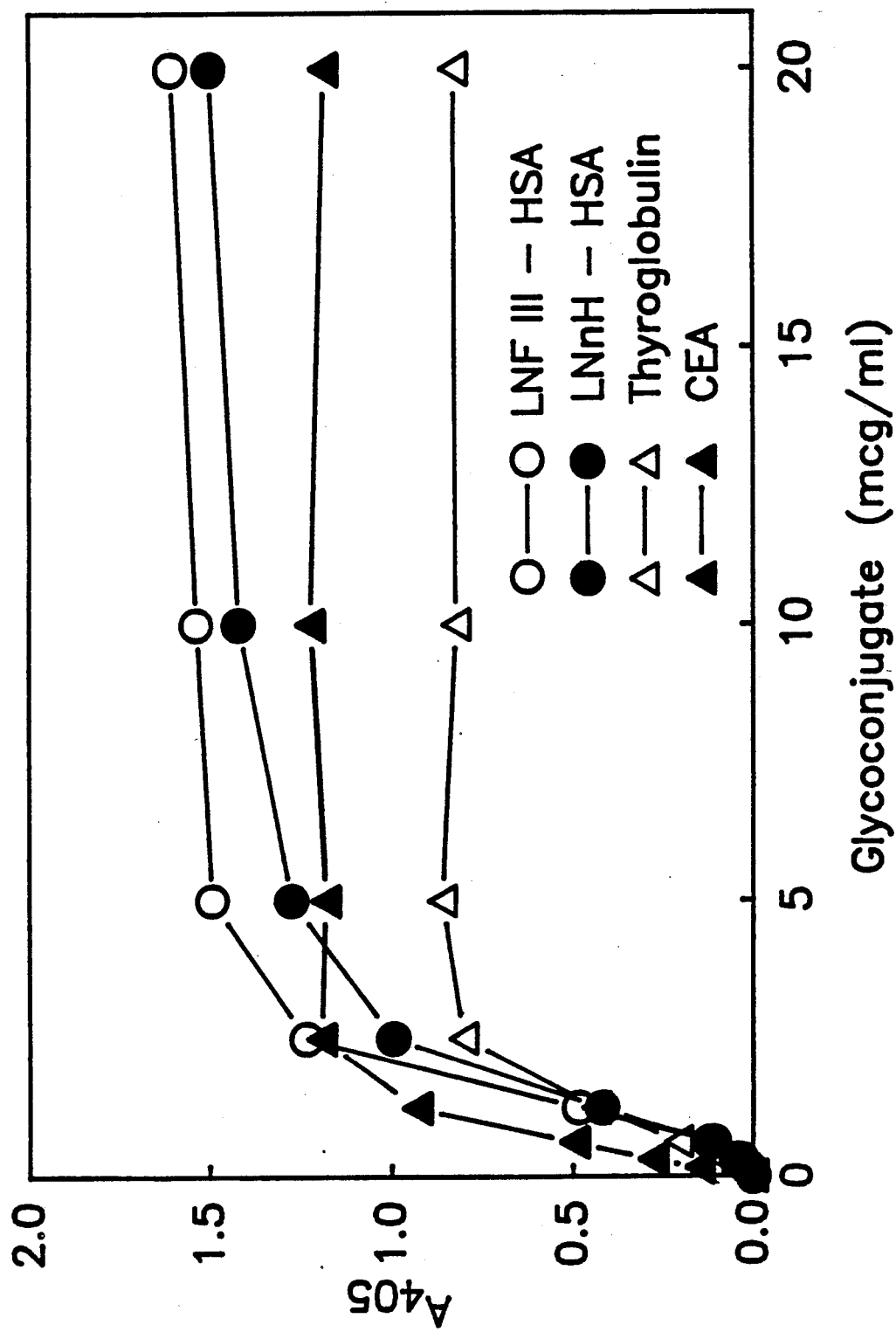
FIG. 3 is a plot of the ELISA of toxin A binding to the following: (i) LNF III-HSA; (ii) a HSA conjugate of the I antigen (LNnH-HSA); (iii) bovine thyroglobulin, which contains the structure Gal$\alpha$(1→3)Gal$\beta$(1→4)GlcNAc; and (iv) human carcinoembryonic antigen (CEA), which contains the X antigen.
Figure 4:
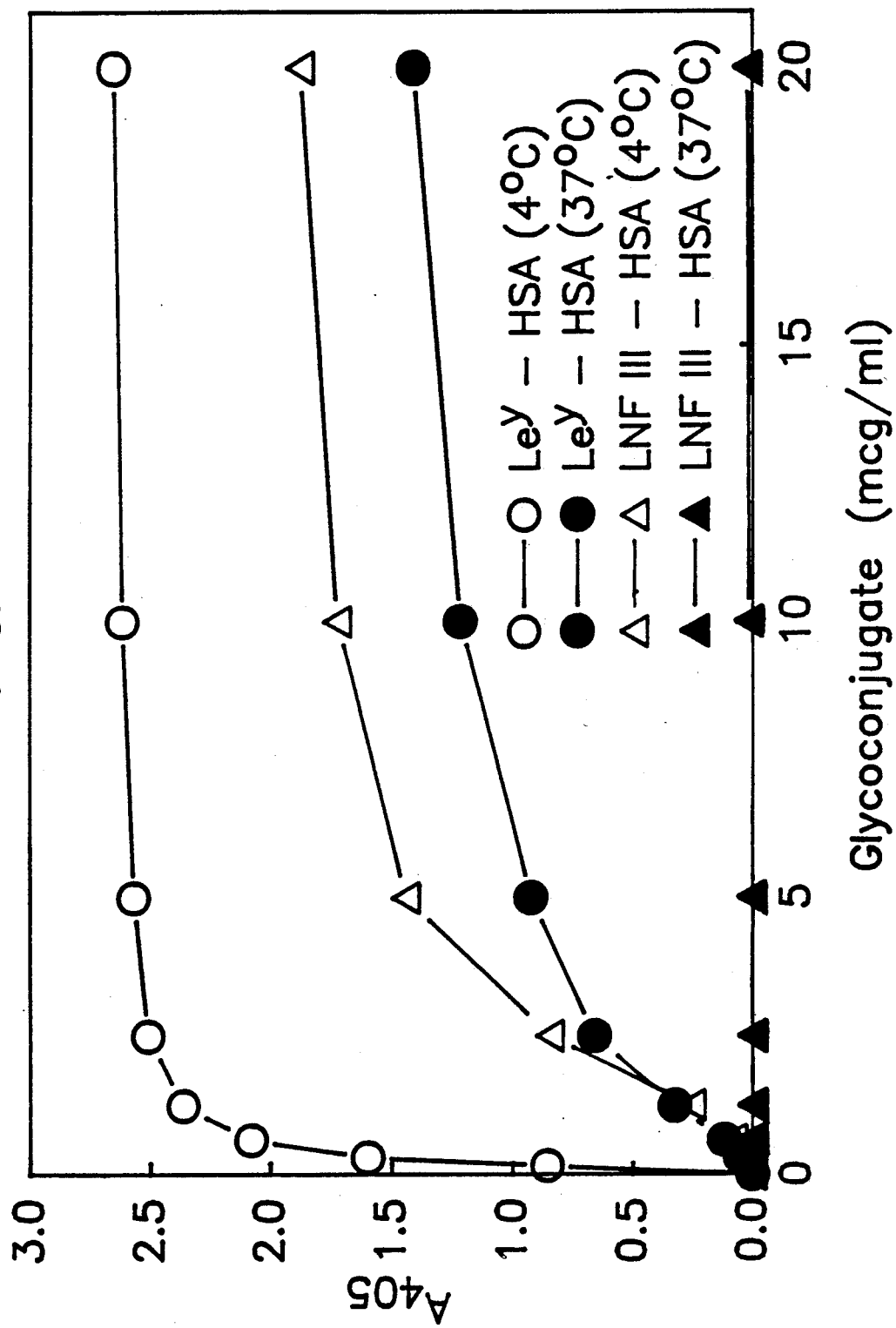
FIG. 4 is a plot of an ELISA of toxin A binding to Le$^Y$-HSA and to LNF III-HSA, at 4° C. and 37° C.
Figure 5:
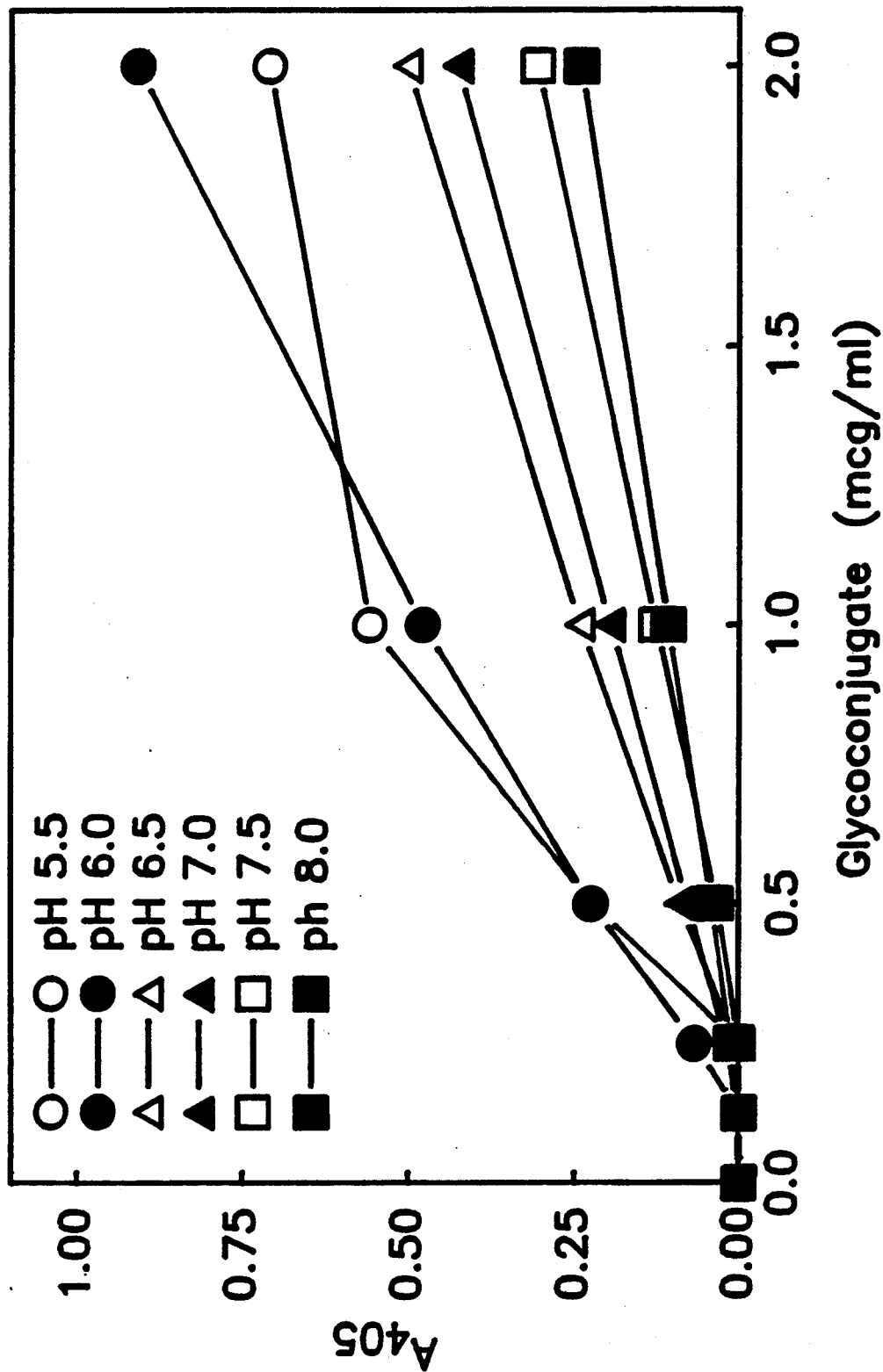
FIG. 5 is a plot of an ELISA of toxin A binding to Le$^Y$-HSA at varying pH. The assay was developed for twenty minutes.
Figure 6A:
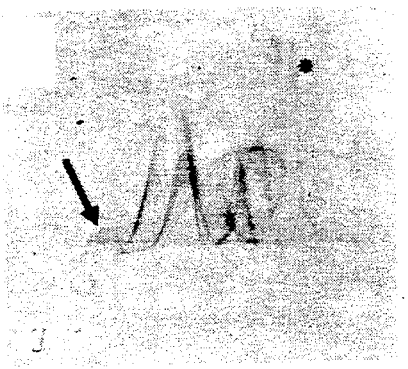
FIG. 6 is a photograph of a stained gel of the crossed immunoelectrophoresis of (A) C. difficile culture filtrate, (B) C. difficile culture filtrate following absorption with immobilized X antigen, and (C) the eluate released by the immobilized X antigen upon heating to 37° C.
Figure 6B:
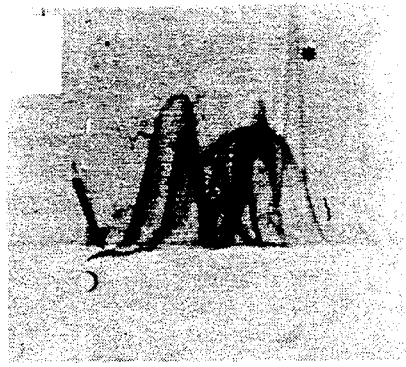
Figure 6C:
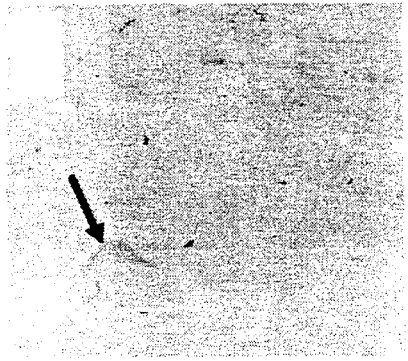

As observed with the crossed immunoelectrophoresis, only the X, Y and I antigens among the oligosaccharide-conjugates reacted with toxin A at 4° C. (Table 1). The ELISA also provides quantitative data for the relative affinity of the receptors for the toxin as shown in FIGS. 3 through 5. Toxin A has a greater affinity for the Y antigen relative to its affinity for the X and I antigens. Moreover, of all the oligosaccharide-HSA conjugates tested, only the Y-HSA conjugate showed significant binding of toxin A at 37° C. The temperature dependence of binding affinity as between the X (LNF III) and Y ($Le^y$) antigens is shown in FIG. 3. The toxin A binding affinity of the X (LNF III) and I (LNnH) antigens is shown in FIG. 4, relative to thyroglobulin and CEA, which contain Galα-(1→3)Galβ(1→4)GlcNAc and the X antigen, respectively.

The pH-dependence of toxin A binding to the Y antigen is shown in FIG. 5. A pH of 6.0 gave the highest absorbance after subtracting the background. This suggests that the optimal pH to bind toxin A to the Y antigen is about pH 6, and the best pH to unbind toxin A to the antigen is about pH 8 or greater.

EXAMPLE 3

Latex Agglutination

In order to confirm the reaction of toxin A with carbohydrates which contain the X and Y antigen structures, the binding of toxin A to chemically synthesized carbohydrate (either the X trisaccharide or Y tetrasaccharide) linked to a latex (Chembiomed Ltd., Edmonton, Canada) was assayed by latex agglutination assay. The antigen-latex reagent was first blocked with 0.5% casein in TBS for 4 hours. 5 μl of antigen-latex reagent was mixed with either 10 μl of toxin A (100 μg/ml) or with 10 μl of PBS on a glass plate. This was incubated once for 2 minutes, then 10 μl of PCG-4, an anti-toxin A monoclonal antibody at 1 mg/ml (Lyerly et al., *J. Clin. Microbiol.* 2; 12-14 (1985)) was added to the mixture. The plate was rocked for 3 minutes, and then observed for agglutination. Latex containing either X or Y antigen were agglutinated by the toxin A/PCG-4 mixtures, but were not agglutinated by the PCG-4 alone.

The preceding experiment, utilizing the chemically synthesized trisaccharide Galβ(1→4)[Fucα(1→3)]GlcNAc and chemically synthesized tetrasaccharide Fucα(1→2)Galβ(1→4)[Fucα(1→3)]GlcNAc, corresponding to the X and Y antigens, respectively, demonstrates that such chemically-synthesized antigens bind toxin A to the same extent as the naturally occurring antigens.

The following example illustrates the purification of toxin A utilizing immobilized X antigen.

EXAMPLE 4

Purification of Toxin A From Culture Filtrate by X-Latex

400 μl of the trisaccharide antigen linked to latex (X-latex, Chembiomed Ltd.) was pelleted by centrifugation yielding a pellet of about 40 μl of latex. To this was added 25 μl of a five-times concentrate of culture filtrate of *Clostridium difficile.* This was mixed and incubated on ice for 10 minutes. The X-latex was pelleted by centrifugation and washed twice with ice cold TBS. To the washed X-latex was then added 25 μl of TBS, which was incubated for 30 minutes at 37° C. The latex was pelleted by centrifugation and the supernatant was collected. Each of the steps were assayed by X-IEP as described in Example 1.

X-IEP assay of the *C. difficile* culture filtrate, prior to absorption with the X-latex is shown in FIG. 6A, revealing a multiplicity of protein components. The arrow points to the protein peak corresponding to toxin A. The peak height is proportional to the concentration of toxin A in the filtrate. The culture filtrate was assayed again following absorption with the X-latex at 4° C. See FIG. 6B. The arrow in FIG. 6B indicates substantial reduction in the presence of toxin A. The material eluted from the X-latex upon heating to 37° C. is assayed in FIG. 6C. The single peak indicated by the arrow corresponds to toxin A. Thus, it was observed that toxin A was selectively purified from all other *Clostridium difficile* proteins, including toxin B (indicated by the star (*) in FIGS. 6A and 6B), demonstrating the specificity of X antigen for binding toxin A.

The present invention provides a simple and rapid method for large-scale purification of *C. difficile* toxin A, or conversely, for purification of materials, such as glycoconjugates or cells, containing the X, Y or I antigens. Toxin A may be conveniently immobilized on a suitable solid substrate to form an affinity matrix for the purification of such materials. A toxin A affinity column for this purpose may be prepared according to Example 17 of U.S. Pat. No. 4,863,852, the entire disclosure of which is incorporated herein by reference. Where the object of the purification technique is to obtain soluble glycoconjugate containing the X, Y or I antigens from cellular materials, the cells are first extracted by suitable detergents, solvents, buffers and the like, to solubilize fractions containing the glycoconjugate. The extract is solubilized and suspended in a suitable liquid and contact with immobilized C. difficile toxin at a temperature favoring reversible binding to the immobilized toxin·A, e.g., 4° C. The glycoconjugate containing the desired antigen binds to the column while the other components of the extract are permitted to pass through the column. The column with the bound glycoconjugate is washed with a suitable buffer, e.g., 0.05M MES, 0.15M NaCl pH 6.0 at 4° C. The temperature is then increased (e.g., 37° C.) to release the bound glycoconjugate, which may be eluted in substantially pure form with a suitable buffer, e.g., 0.05M MOPS, 0.15M NaCl pH 8.0.

Toxin A may be used to detect the presence of the X, Y or I antigens in specimens of interest. In particular, toxin A may be utilized as a reagent in a histochemical assay to detect any of these antigens in thinly sliced sections of tissue. Such histochemical assay methods are known to those skilled in the art.

All references herein cited with respect to synthetic or analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method for detecting *Clostridium difficile* toxin A comprising:

(a) contacting a specimen with a reagent comprising one or more of the following terminal non-reducing structures (i)

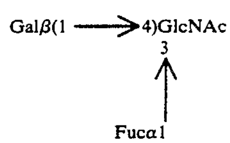

(ii)

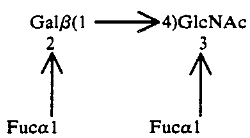

(iii)

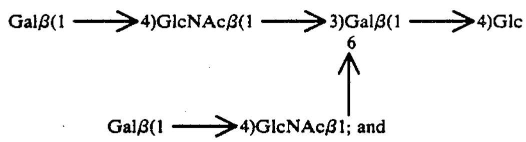

and (b) assaying for binding of *Clostridium difficile* toxin A to the reagent.

2. A method according to claim 1 wherein the reagent contains the structure

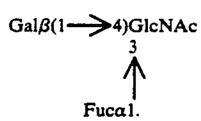

3. A method according to claim 2 wherein the reagent contains the structure

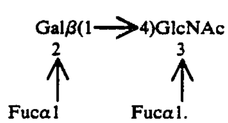

4. A method according to claim 1 wherein the reagent contains the structure

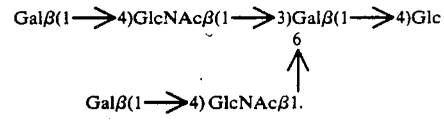

5. A method according to claim 1 wherein the reagent comprises the terminal non-reducing structure conjugated to a carrier.

6. A method according to claim 5 wherein the carrier comprises human serum albumin.

7. A method according to claim 1 wherein the assay means of step (b) is selected from the group consisting of enzyme-linked immunosorbent assay, latex agglutination, and crossed immunoelectrophoresis.

8. A method according to claim 1 comprising the steps of:

adhering said reagent to a solid support;

incubating the adhered reagent with the specimen to immobilize the toxin A in the specimen thereto;

contacting the immobilized toxin A with an enzyme-labelled anti-toxin A antibody and a substrate for the enzyme; and determining the amount of toxin A in the specimen from the extent of enzymatic conversion of the substrate.

9. A method according to claim 1 comprising the steps of:

incubating the specimen with anti-toxin A antibody adhered to a solid support to immobilize the toxin A contained therein;

incubating the immobilized toxin A with a reagent comprising said terminal non-reducing structure linked to a carrier;

contacting the immobilized toxin A with an enzyme-labelled antibody to the carrier and a substrate for the enzyme; and determining the amount of toxin A in the specimen from the extent of enzymatic conversion of the substrate.

10. A method according to claim 9 wherein the carrier comprises human serum albumin.

11. A method according to claim 1 wherein the reagent comprises the structure 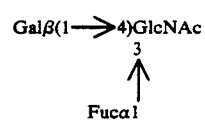 or 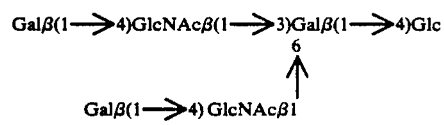 and contact in step (a) is at a temperature from about 0° C. to about 15° C.

12. A method according to claim 1 wherein the reagent comprises the structure $$\begin{array}{c} \text{Gal}\beta(1\longrightarrow 4)\text{GlcNAc} \\ 2\phantom{XXXXX}3 \\ \uparrow\phantom{XXXXX}\uparrow \\ \text{Fuc}\alpha 1\phantom{XX}\text{Fuc}\alpha 1 \end{array}$$

and contact in step (a) is at a temperature from about 0° C. to about 37° C.

13. A method according to claim 12 wherein the pH of step (b) is about 6.

14. A method of isolating or purifying *Clostridium difficile* toxin A comprising:

(a) contacting a source of toxin A with an immobilized reagent containing a terminal non-reducing structure selected from the group of structures consisting of $$\begin{array}{c} \text{Gal}\beta(1\longrightarrow 4)\text{GlcNAc} \\ 3 \\ \uparrow \\ \text{Fuc}\alpha 1 \end{array} \qquad \text{(i)}$$

$$\begin{array}{c} \text{Gal}\beta(1\longrightarrow 4)\text{GlcNAc} \\ 2\phantom{XXXXX}3 \\ \uparrow\phantom{XXXXX}\uparrow \\ \text{Fuc}\alpha 1\phantom{XX}\text{Fuc}\alpha 1 \end{array} \qquad \text{(ii)}$$

$$\begin{array}{c} \text{Gal}\beta(1\longrightarrow 4)\text{GlcNAc}\beta(1\longrightarrow 3)\text{Gal}\beta(1\longrightarrow 4)\text{Glc} \\ 6 \\ \uparrow \\ \text{Gal}\beta(1\longrightarrow 4)\text{GlcNAc}\beta 1 \end{array} \qquad \text{(iii)}$$

at a temperature favoring reversible binding of toxin A to the immobilized reagent.

(b) increasing the temperature or pH to release toxin A bound to the immobilized reagent;

(c) eluting toxin A.

15. A method according to claim 14 herein the temperature in step (a) is below about 20° C.

16. A method according to claim 15 wherein the temperature in step (a) is from about 0° C. to about 15° C.

17. A method according to claim 16 wherein the temperature is increased in step (b) to above about 30° C.

18. A method according to claim 17 wherein the temperature is increased in step (b) to between about 30° C. and about 37° C.

19. A method according to claim 14 wherein the reagent is immobilized on a subs&rate to form an affinity column.

20. A method according to claim 14 wherein the immobilized reagent contains the structure $$\begin{array}{c} \text{Gal}\beta(1\longrightarrow 4)\text{GlcNAc} \\ 2\phantom{XXXXX}3 \\ \uparrow\phantom{XXXXX}\uparrow \\ \text{Fuc}\alpha 1\phantom{XX}\text{Fuc}\alpha 1. \end{array}$$

21. A method according to claim 18 wherein the source of toxin A is contacted with the immobilized reagent at a pH of about 6 to bind the toxin A to the reagent, and the toxin A is released from the immobilized reagent by increasing the pH to at least about 8.

* * * * *